United States Patent
Chang et al.

(10) Patent No.: US 9,925,293 B2
(45) Date of Patent: Mar. 27, 2018

(54) SOLUTION FOR TREATING CONTACT LENS

(71) Applicant: PEGAVISION CORPORATION, Taoyuan (TW)

(72) Inventors: Han-Yi Chang, Taoyuan (TW); Ya-Hsuan Liao, Taoyuan (TW); Shu-Chen Lu, Taoyuan (TW); Ya-Hui Chang, Taoyuan (TW); Yu-Chin Lai, Taoyuan (TW)

(73) Assignee: PEGAVISION CORPORATION, Taoyuan (TW)

( * ) Notice: Subject to any disclaimer, the term of this patent is extended or adjusted under 35 U.S.C. 154(b) by 0 days.

(21) Appl. No.: 15/256,637

(22) Filed: Sep. 5, 2016

(65) Prior Publication Data

US 2017/0368221 A1 Dec. 28, 2017

(30) Foreign Application Priority Data

Jun. 27, 2016 (TW) .................................. 105120216

(51) Int. Cl.

| | |
|---|---|
| *A61L 12/14* | (2006.01) |
| *C08F 130/02* | (2006.01) |
| *C11D 3/00* | (2006.01) |
| *C11D 3/04* | (2006.01) |
| *C11D 3/16* | (2006.01) |
| *C11D 3/36* | (2006.01) |
| *C11D 3/37* | (2006.01) |
| *A61K 9/00* | (2006.01) |
| *A61K 47/32* | (2006.01) |
| *A61K 9/08* | (2006.01) |
| *C11D 7/10* | (2006.01) |

(52) U.S. Cl.
CPC ............ *A61L 12/14* (2013.01); *A61K 9/0048* (2013.01); *A61K 9/08* (2013.01); *A61K 47/32* (2013.01); *C08F 130/02* (2013.01); *C11D 3/0078* (2013.01); *C11D 3/042* (2013.01); *C11D 3/046* (2013.01); *C11D 3/168* (2013.01); *C11D 3/365* (2013.01); *C11D 3/3784* (2013.01); *C11D 7/10* (2013.01)

(58) Field of Classification Search
CPC ................................ C08K 5/0058; C08L 39/00
See application file for complete search history.

(56) References Cited

U.S. PATENT DOCUMENTS

| | | | | |
|---|---|---|---|---|
| 5,300,296 | A | * | 4/1994 | Holly .................... A01N 33/12 424/427 |
| 9,295,747 | B2 | | 3/2016 | Matsuoka et al. |
| 2003/0186825 | A1 | | 10/2003 | Mitani et al. |
| 2004/0057980 | A1 | | 3/2004 | Wagenaar |
| 2006/0217276 | A1 | | 9/2006 | Mitani et al. |
| 2007/0104744 | A1 | | 5/2007 | Smith |
| 2009/0100801 | A1 | | 4/2009 | Zhao et al. |
| 2013/0276407 | A1 | | 10/2013 | Zhao |

FOREIGN PATENT DOCUMENTS

| | | | | |
|---|---|---|---|---|
| CN | 1281283 | C | | 10/2006 |
| CN | 104272174 | A | | 1/2015 |
| EP | 3040085 | A1 | | 7/2016 |
| JP | H10324634 | A | | 12/1998 |
| JP | 2000-098310 | A | | 4/2000 |
| JP | 2000-347141 | A | | 12/2000 |
| JP | 2012-088524 | A | * | 5/2010 ............. G02C 13/00 |
| WO | 2002062260 | A2 | | 8/2002 |
| WO | WO02062260 | A | * | 8/2002 |
| WO | 2008086270 | A3 | | 7/2008 |

* cited by examiner

*Primary Examiner* — Anna Falkowitz
(74) *Attorney, Agent, or Firm* — CKC & Partners Co., Ltd.

(57) ABSTRACT

A solution for treating contact lens is provided. The solution includes about 0.01-1.0 parts by weight (pbw) of a polymer having phosphorylcholine groups, about 0.01-1 pbw of an inorganic salt, and about 100 pbw of water. The polymer has a number-average molecular weight of about 4,000 to about 1,000,000 daltons and has a structure of formula (I):

(I)

$$\left[\begin{array}{c}CH_3 \\ \vert \\ -CH_2-C- \\ \vert \\ C=O \\ \vert \\ O \\ \vert \\ CH_3\end{array}\right]_m \left[\begin{array}{c} \\ -CH_2-C- \\ \vert \\ C=O \\ \vert \\ O-R\end{array}\right]_n \begin{array}{c}O^{\ominus} \\ \vert \\ -O-P-O-CH_2CH_2-N^{\oplus}(CH_3)_3 \\ \vert \vert \\ O\end{array}$$

wherein, in formula (I), m is a positive integer, n is zero or a positive integer, and R is $C_2$-$C_{12}$ alkyl group or $C_2$-$C_{12}$ hydroxyalkyl group. When n is a positive integer, m/n is greater than 1.

9 Claims, No Drawings

SOLUTION FOR TREATING CONTACT LENS

CROSS-REFERENCE TO RELATED APPLICATION

This application claims priority to Taiwan Application Serial Number 105120216, filed Jun. 27, 2016, which is herein incorporated by reference.

BACKGROUND

Field of Invention

The present invention relates to a solution for treating contact lens.

Description of Related Art

Soft contact lens is a kind of popular commercial product. It is packed inside a polypropylene blister package including storage solution for sale. The storage solution is usually a buffered saline solution which includes sodium chloride and other inorganic salts. In addition, it further includes surfactants and/or moisturizers to keep the contact lens moist and prevent the contact lens from sticking on the inner surface of blister-like structure of blister package.

Regarding to functions of contact lens, the contact lens must be capable of correcting visual acuity. In addition, a comfort level of wearing contact lens would affect consumer preferences. Therefore, in the field of contact lens, people in the business target promoting the comfort level of wearing contact lens. The comfort level of wearing contact lens is affected by a lot of factors. For example, discomfort generated from wearing contact lens may be because lens is too rigid, lens has poor wettability and thus make surfaces of lens dry, surfaces of lens are rough, or lens is not well-designed.

The wettability and the comfort level of lens depend on the materials of lens. Besides, they depend on storage solution of lens and even the components of cleaning solution. Therefore, the solution is added with hydrophilic substances to increase the wettability of lens such that surfaces of lens are not easy to become dry, in addition, it is necessary that the solution is added with some nutrients to boost eye health. However, there is a lack of treating solution containing both hydrophilic substances and nutrients for contact lens in the market.

Accordingly, a treating solution for contact lens containing both hydrophilic substances and nutrients is in need. It should be capable of promoting wettability of contact lens such that surfaces of contact lens are not easy to become dry, boosting eye health to reduce eyestrain caused by wearing lens for long periods of time, and promoting comfort level of wearing contact lens.

SUMMARY

The invention provides a solution for treating contact lens. The solution includes about 0.01-1.0 parts by weight (pbw) of a polymer having phosphorylcholine groups, about 0.01-1 pbw of an inorganic salt, and about 100 pbw of water. The polymer has a number-average molecular weight of about 4,000 to about 1,000,000 daltons and has a structure of formula (I):

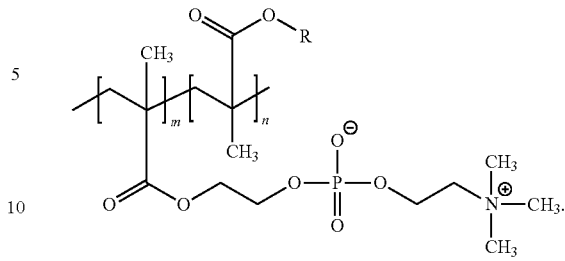

In formula (I), m is a positive integer, n is zero or a positive integer, and R is $C_2$-$C_{12}$ alkyl group or $C_2$-$C_{12}$ hydroxyalkyl group. When n is a positive integer, m/n is greater than 1. By making the solution for treating contact lens include the hydrophilic polymer, the wettability of contact lens can be promoted such that surfaces of lens are not easy to become dry and the eyestrain caused by wearing lens can be reduced. According to patent literatures, when hydrophilic polymers, such as hyaluronic acid, are added in a solution for treating contact lens, the solution can achieve the effect of moistening contact lens. In the present invention, we observe that surfaces of lenses are not easy to become dry when subjects wear lenses which have been immersed in the solution including the polymer having phosphorylcholine groups.

In some embodiments of the invention, the solution further includes about 0.001-0.1 pbw of vitamin B. In some embodiments of the invention, the vitamin B is selected from the group consisting of vitamin B1, vitamin B2, vitamin B3, vitamin B6, and vitamin B12.

In some embodiments of the invention, an amount of the vitamin B6 is in a range of about 0.01-0.1 pbw.

In some embodiments of the invention, an amount of the vitamin B12 is in a range of about 0.001-0.1 pbw.

In some embodiments of the invention, R is n-butyl, 2-ethylhexyl, isodecyl, lauryl, 2-hydroxyethyl, or 2,3-dihydroxypropyl.

In some embodiments of the invention, the inorganic salt includes about 0.1-1 pbw of sodium chloride.

In some embodiments of the invention, the solution further includes about 0.1-1 pbw of boric acid.

In some embodiments of the invention, the solution further includes about 0.01-0.1 pbw of sodium borate.

In some embodiments of the invention, the solution is a solution for storing contact lens or a solution for cleaning contact lens.

DETAILED DESCRIPTION

The following embodiments are disclosed for detailed description. For illustration clarity, many details of practice are explained in the following descriptions. However, it should be understood that these details of practice do not intend to limit the present invention. That is, these details of practice are not necessary in parts of embodiments of the present invention. Furthermore, chemical formulas in the invention are shown with schematic illustrations.

The terminology used herein is for the purpose of describing particular embodiments only and is not intended to be limiting of the invention. As used herein, the singular forms "a", "an" and "the" are intended to include the plural forms as well, unless the context dearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

As mentioned above, the wettability and the comfort level of lens are closely related to both storage solution of lens and the components of cleaning solution. That is because some components in storage solution can enter into the lens matrix or stay near lens surface during autoclaving at high temperature. Further, because of these factors, pore sizes and hydrophilicity of lens and the difference between the polarity of lens and the polarity of components in the storage solution, the components in the storage solution have different degrees of adhesion on the surfaces of lens.

While different hydrogel lenses may have the same water contents, they may be formed from combinations of different monomers and thus have different crosslinking densities. Accordingly, the ability of components of storage solution to enter or penetrate into the lens is very much dependent on the polarities and the molecular weights of these components as well as crosslinking densities of the hydrogel lens.

Common polymers for forming contact lenses can be polymerized by ethylenically-based polymerizable monomers and prepolymers including silicon. The polymers includes N-vinyl pyrrolidone (NVP), N,N-dimethyl acrylamide (DMA), 2-methacryloyloxyethyl phosphorylcholine (MPC), different kinds of alkyl methacrylate, different kinds of hydroxyalkyl methacrylate and so on.

Hydrophilic properties of different ethylenically-based polymerizable monomers are different. Because the polymer formed by suitable ethylenically-based polymerizable monomers has hydrophilic property, it can be added in the solution for treating contact lens, which is the solution for storing contact lens or the solution for cleaning contact lens, to promote the wettability of contact lens.

However, even thought the hydrophilic polymers can promote the wettability of contact lens, the effects of keeping the comfort feeling during a long wearing time are limited. Therefore, in addition to the hydrophilic polymers, the storage solution and the cleaning solution are necessary to be added with additional components to prevent the surfaces of lens from dryness and promote the comfort level during a long wearing time. Accordingly, the present disclosure provides a solution for treating contact lens. It includes a polymer having phosphorylcholine groups or includes the polymer and vitamin B at the same time to achieve the effects of reducing eyestrain and keeping the wettability of lens to prevent surfaces of lens from dryness simultaneously.

The compound, 2-methacryloyloxyethyl phosphorylcholine (MPC), has a phosphorylcholine group and thus has an excellent hydrophilic property. Therefore, homopolymers or copolymers, these polymers formed from the compounds all have excellent hydrophilic properties as well.

In regard to the homopolymer, poly[2-methacryloyloxyethyl phosphorylcholine] (poly-MPC) having phosphorylcholine groups is a highly hydrophilic polymer. In regard to the copolymer, because of high hydrophilicity of MPC group, the copolymer copolymerized by MPCs and methacrylate monomers would also have excellent hydrophilic property. Therefore, homopolymers or copolymers, if these polymers formed from MPCs are added into a solution for treating contact lens, these polymers can effectively increase the wettability of lens.

On the other hand, vitamin Bs, especially vitamin B6 (pyridoxine) and vitamin B12 (cobalamin), have remarkable effects of health promotion for human eyes.

In addition to regulating various sulfur-containing amino acids metabolism, promoting the glycogen decomposition, keeping balance between sodium ions and potassium ions, and promoting erythropoiesis, vitamin B6 can enhance immunity and promote cell growth. Further, vitamin B6 also can promote the synthesis of co-enzyme A and the absorption of vitamin B12, so vitamin B6 can regulate brain cell metabolism and thus has the effects of strengthening the nervous system and stabilizing emotions.

Vitamin B12 and folic acid concurrently regulate the concentration of homocysteine to avoid heart disease risk and stroke risk caused by too much homocysteine and reduce osteoporosis risk and Alzheimer's disease risk. Further, vitamin B12 is very important to maintain normal functions of nerve and can be used to reduce eyetrain.

Furthermore, in addition to vitamin B6 and vitamin B12, vitamin B1, B2, and B3 also have effects on nerves and eye health. Vitamin B1 and vitamin B3 (Niacin) can be used to prevent nystagmus, slow visual reaction, or eyetrain. Vitamin B2 can prevent dry eye, conjunctival hyperemia, photophobia, itching, eyestrain, and even optic neuritis or keratitis. Accordingly, the solution for treating contact lens may include vitamins B6, B12, B1, B2, B3, or a combination thereof to promote eye comfort.

The polymer having phosphorylcholine groups and vitamin B can stay near lens surface or release from lens matrix, so lens surface is highly moist and thus can reduce dryness caused by wearing lens for a long time. Besides, vitamins B6, B12 can nourish eyes at the same time.

Therefore, the invention provides a solution for treating contact lens. The solution includes about 0.01-1.0 parts by weight (pbw) of a polymer having phosphorylcholine groups, about 0.01-1 pbw of an inorganic salt, and about 100 pbw of water. The polymer has a number-average molecular weight of about 4,000 to about 1,000,000 daltons and has a structure of formula (I):

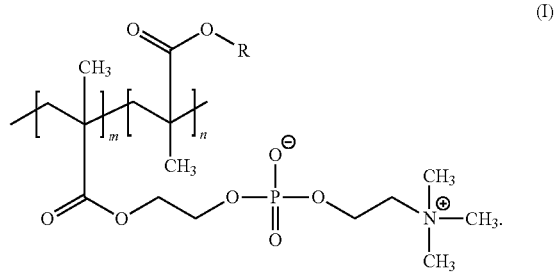

In formula (I), m is a positive integer, n is zero or a positive integer, and R is $C_2$-$C_{12}$ alkyl group or $C_2$-$C_{12}$ hydroxyalkyl group. When n is a positive integer, m/n is greater than 1.

When n is zero, this polymer is a homopolymer having phosphorylcholine groups. That is, the homopolymer is poly(2-methacryloyloxyethyl phosphorylcholine)(poly-MPC). When n is a positive integer, this polymer is a copolymer having phosphorylcholine groups.

The copolymer of present invention may be copolymerized by 2-methacryloyloxyethyl phosphorylcholines (MPC) and methacrylic acid esters. For example, the methacrylic acid ester may be alkyl methacrylate or hydroxyalkyl methacrylate. The alkyl methacrylate has $C_2$-$C_{12}$ alkyl group. It may be n-butyl methacrylate (BMA), 2-ethylhexyl methacrylate (EHMA), isodecyl methacrylate (IDMA) or lauryl methacrylate (LMA). The hydroxyalkyl methacrylate has $C_2$-$C_{12}$ hydroxyalkyl group. It may be 2-hydroxyethyl methacrylate (HEMA) or 2,3-dihydroxypropyl methacrylate (DHPM). Therefore, in the polymer having the structure of formula (I), R is n-butyl, 2-ethylhexyl, isodecyl, lauryl, 2-hydroxyethyl, or 2,3-dihydroxypropyl.

In some embodiments of the invention, the solution for treating contact lens further includes about 0.001-0.1 pbw of vitamin B. In some embodiments of the invention, the vitamin B is selected from the group consisting of vitamin B1, vitamin B2, vitamin B3, vitamin B6, and vitamin B12. In some embodiments of the invention, an amount of the vitamin B6 is in a range of about 0.01-0.1 pbw. In some embodiments of the invention, an amount of the vitamin B12 is in a range of about 0.001-0.1 pbw.

In some embodiments, when the solution for treating contact lens includes vitamin B12, the solution shows the color pink. Because a portion of vitamin B12 would stay on surfaces of lens or enter lens matrix, the lens would show the color light pink. The shades of the color pink depend on the amount of vitamin B12 in lens.

In some embodiments of the invention, the inorganic salt includes about 0.1-1 pbw of sodium chloride. The about 0.1-1 pbw of sodium chloride may dissolves in water to form normal saline. In some embodiments, the solution for treating contact lens further includes about 0.1-1 pbw of boric acid in addition to sodium chloride. In other embodiments, the solution further includes about 0.01-0.1 pbw of sodium borate. The boric acid and the sodium borate both are capable of adjusting the pH value of the solution and have antimicrobial activity.

In some embodiments, the solution for treating contact lens of the present invention is a solution for storing contact lens, namely contact lens packaging solution, or a solution for cleaning contact lens, namely contact lens cleaning solution. In some embodiments, the solution for treating contact lens of the present invention may selectively includes surfactants and/or moisturizers.

The solution for treating contact lens of the present invention may be applied to general hydrogel lens. Moreover, the number-average molecular weight and the amount of the polymer can be adjusted, such that the solution can be applied to different hydrogel lens or silicone hydrogel lens to prevent wearer's eyes from feeling dry, thereby promoting the comfort level of wearer.

The following Examples are provided to illustrate certain aspects of the present disclosure and to aid those of skill in the art in practicing this disclosure. These Examples are in no way to be considered to limit the scope of the disclosure in any manner.

Experiment 1: Preparing Homopolymer Having Phosphorylcholine Groups—Poly(2-Methacryroyloxyethylphosphoryl-Choline (MPC) to Obtain Examples 1A-1C The Experiment 1 included the following steps. 50 g (0.169 moles) of MPC and 150 mL of methanol were added into a three-neck round-bottom flask equipped with a reflux condenser. Nitrogen gas was injected into the three-neck round-bottom flask. The MPC and the methanol were stirred under the nitrogen-filled environment for 10 minutes until dissolution. Subsequently, 0.25 g of azobisisobutyronitrile (AIBN) and 0.0398 g (0.509 mmoles) of 2-mercaptoethanol were added and then heated to 45° C. maintaining for 24 hours. The AIBN is a polymerization initiator and it can bond to the carbon atom which is connected with double bonds in methacryloyloxyethyl of MPC to initiate free radical polymerization. The 2-mercaptoethanol is a chain transfer agent and it is capable of making the terminals of chain polymer having radical terminate reaction and thus the length and the molecule weight (number-average molecular weight and weight-average molecular weight) of a polymer can be controlled. After that, the methanol was stripped. The formed product, poly-MPC (Example 1A), was crushed into powder and dried in an oven at 100° C. for 6 hours. Through this experiment, 45 g of poly-MPC (Example 1A), which is MPC homopolymer, was produced. It was characterized by gel permeation chromatography (GPC) to obtain the number-average molecular weight ($M_n$) and the weight-average molecular weight ($M_w$).

The number-average molecular weight ($M_n$) can be obtained by measuring the molecular mass of n polymer molecules, summing the masses, and dividing by n. The weight-average molecular weight ($M_w$) can be obtained by measuring each polymer molecule's molecular weight, multiplying each molecular weight with each polymer molecule's weight percent relative to the total weight of all polymer molecules, and summing these products. Because when calculating the $M_n$, the weights of polymer molecules with different numbers of monomers are same; however, when calculating the $M_w$, the weights of heavier polymer molecules are larger, $M_w$ of polymers is usually larger than $M_n$. The ratio of $M_w$ to $M_n$ is polydispersity. Generally, if adding less 2-mercaptoethanol during polymerization, the polydispersity would be higher. It shows that the distribution of molecular weights of polymers is wider. The standard deviation between the numbers of monomers in polymers is larger.

Other homopolymers were also made by the method described above but the amount of each reacts was different. In details, the preparation of MPC homopolymers included the following steps. 59 g (0.1999 moles) of MPC and 250 mL of methanol were added into a three-neck round-bottom flask equipped with a reflux condenser. Nitrogen gas was injected into the three-neck round-bottom flask. The MPC and the methanol were stirred under the nitrogen-filled environment for 10 minutes until dissolution. Subsequently, 0.295 g of azobisisobutyronitrile (AIBN) and 2-mercaptoethanol were added and then heated to 45° C. maintaining for 24 hours. The amount of 2-mercaptoethanol was 0.2343 g (3 mmoles) or 0.0398 g (0.5 mmoles). Therefore, due to different amounts of 2-mercaptoethanol, the final products, Example 1B and Example 1C, could be produced respectively. After that, the methanol was stripped. The formed products, poly-MPCs (Example 1B and Example 1C), were dried in an oven at 100° C. for 6 hours. The MPC homopolymers produced by the experiment were characterized by GPC.

The results characterized by GPC show that: Example 1A, which was formed from 50 g of MPC and 0.5 mmoles of 2-mercaptoethanol, has a number-average molecular weight ($M_n$) of 9,604, a weight-average molecular weight ($M_w$) of 31,935, and a polydispersity of 3.32. Example 1B, which was formed from 59 g of MPC and 3 mmoles of 2-mercaptoethanol, has a number-average molecular weight ($M_n$) of 17,646, a weight-average molecular weight ($M_w$) of 45,791, and a polydispersity of 2.595. Example 1C, which was formed from 59 g of MPC and 0.5 mmoles of 2-mercaptoethanol, has a number-average molecular weight ($M_n$) of 47,121, a weight-average molecular weight ($M_w$) of 206,531, and a polydispersity of 4.383.

Examples 1A-1C have a structure of formula (II) as follows:

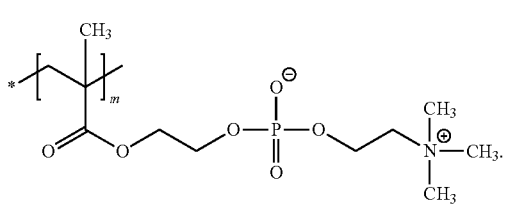
(II)

In formula (II), m is a positive integer and * is the starting point of the polymerization. That is, * is the position connecting with AIBN.

Experiment 2: Preparing Copolymer Having Phosphorylcholine Groups to Obtain Examples 2A-2D MPC copolymers were also made by the method described above but MPC copolymers were polymerized by different kinds of hydroxyalkyl methacrylate monomers. Moreover, the amount of each reactant was different. In details, the preparation of MPC polymers included the following steps. 48 g (0.163 moles) of MPC, 12 g (0.092 moles) of 2-hydroxyethyl methacrylate (HEMA), and 250 mL of methanol were added into a three-neck round-bottom flask equipped with a reflux condenser. Nitrogen gas was injected into the three-neck round-bottom flask. The MPC, the HEMA and the methanol were stirred under the nitrogen-filled environment for 10 minutes until dissolution. Subsequently, 0.295 g of azobisisobutyronitrile (AIBN) and 2-mercaptoethanol were added and then heated to 45° C. maintaining for 24 hours. The amount of 2-mercaptoethanol was 0.932 g (0.012 moles), 0.2343 g (3 mmoles), or 0.0469 g (0.06 mmoles). Therefore, due to different amounts of 2-mercaptoethanol, the final products, Example 2A, Example 2B, and Example 2C, could be produced respectively. After that, the methanol was stripped. The formed products, MPC-HEMA copolymers (Examples 2A-2C), namely poly(MPC-co-HEMA)s, were dried in an oven at 100° C. for 6 hours. The MPC-HEMA copolymers produced by the experiment were characterized by GPC to obtain number-average molecular weights ($M_n$) and weight-average molecular weights ($M_w$).

The results characterized by GPC show that: Example 2A, which was formed from HEMA and 0.012 moles of 2-mercaptoethanol, has a number-average molecular weight ($M_n$) of 13,341, a weight-average molecular weight ($M_w$) of 21,438, and a polydispersity of 1.607. Example 2B, which was formed from HEMA and 3 mmoles of 2-mercaptoethanol, has a number-average molecular weight ($M_n$) of 29,326, a weight-average molecular weight ($M_w$) of 123,345, and a polydispersity of 4.206. Example 2C, which was formed from HEMA and 0.06 mmoles of 2-mercaptoethanol, has a number-average molecular weight ($M_n$) of 106,978, a weight-average molecular weight ($M_w$) of 721,246, and a polydispersity of 6.742. Examples 2A-2C have a structure of formula (III) as follows:

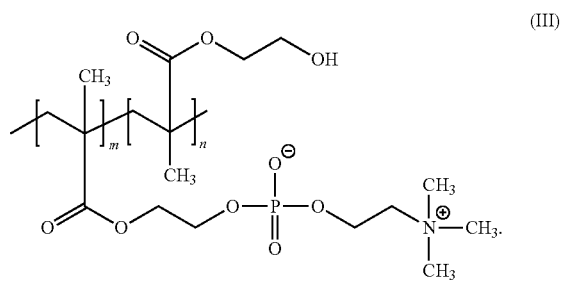
(III)

In formula (III), m and n are positive integers and * is the starting point of the polymerization. That is, * is the position connecting with AIBN.

Further, Example 2D was also made by the method described above. However, the HEMA was replaced with 5 g (0.0352 moles) of n-butyl methacrylate (BMA) and the amount of AIBN was adjusted to 0.1 g, the amount of 2-mercaptoethanol was adjusted to 0.0615 g (0.8 mmoles), the amount of methanol was adjusted to 284 mL. MPC-BMA copolymer (Example 2D), namely poly(MPC-co-BMA), could be produced.

Example 2D, which was formed from BMA and 0.8 mmoles of 2-mercaptoethanol, has a number-average molecular weight ($M_n$) of 35,041, a weight-average molecular weight ($M_w$) of 74,286, and a polydispersity of 2.12. Example 2D has a structure of formula (IV) as follows:

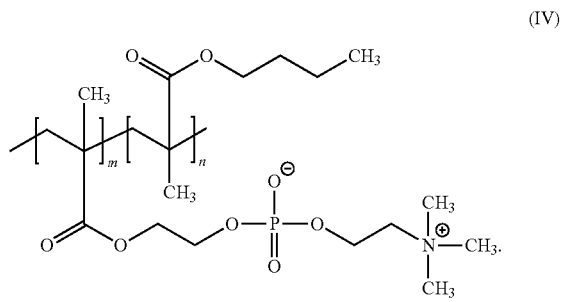
(IV)

In formula (IV), m and n are positive integers and * is the starting point of the polymerization. That is, * is the position connecting with AIBN.

The reactants used for producing Examples 1A-1C and 2A-2D and the molecular weights and the polydispersities of Examples 1A-1C and 2A-2D are all listed in the following Table 1:

TABLE 1

|  | Example 1A | Example 1B | Example 1C | Example 2A | Example 2B | Example 2C | Example 2D |
| --- | --- | --- | --- | --- | --- | --- | --- |
| MPC | 50 g (0.169 mole | 59 g (0.1999 mole) | 59 g (0.1999 mole) | 48 g (0.163 mole) | 48 g (0.163 mole) | 48 g (0.163 mole) | 45 g (0.153 mole) |
| HEMA | — | — | — | 12 g (0.092 mole) | 12 g (0.092 mole) | 12 g (0.092 mole) | — |

TABLE 1-continued

| | Example 1A | Example 1B | Example 1C | Example 2A | Example 2B | Example 2C | Example 2D |
|---|---|---|---|---|---|---|---|
| BMA | — | — | — | — | — | — | 5 g (0.0352 mole) |
| 2-Mercaptoethanol | 0.0398 g (0.509 mmole) | 0.2343 g (3 mmole) | 0.0398 g (0.5 mmole) | 0.932 g (0.012 mole) | 0.2343 g (3 mmole) | 0.0469 g (0.06 mmole) | 0.0615 g (0.8 mmole) |
| AIBN | 0.25 g | 0.295 g | 0.295 g | 0.295 g | 0.295 g | 0.295 g | 0.1 g |
| Methanol | 150 mL | 250 mL | 250 mL | 250 mL | 250 mL | 250 mL | 284 mL |
| Number-average molecular weight ($M_n$) | 9,604 | 17,646 | 47,121 | 13,341 | 29,326 | 106,978 | 35,041 |
| Weight-average molecular weight ($M_w$) | 31,935 | 45,791 | 206,531 | 21,438 | 123,345 | 721,246 | 74,286 |
| Polydispersity | 3.32 | 2.595 | 4.383 | 1.607 | 4.206 | 6.742 | 2.12 |

Experiment 3: Preparing Lens Storage Solutions Including MPC Hopolymers and/or Vitamin B This experiment was performed by selectively adding Example 1 (poly-MPC), hyaluronic acid, vitamin B6, and/or vitamin B12 to form six different contact lens storage solutions, namely Comparative Examples 3A-3B and Examples 3C-3F. Components of Each of Comparative Examples 3A-3B and Examples 3C-3F are listed as follows.

Comparative Example 3A included 0.708% w/w of sodium chloride, 0.470% w/w of boric acid, 0.05% w/w of sodium borate, and water as solvent.

Comparative Example 3B included 0.708% w/w of sodium chloride, 0.470% w/w of boric acid, 0.05% w/w of sodium borate, 0.10% w/w of hyaluronic acid (HA) which has a number-average molecular weight of 100,000, and water as solvent.

Example 3C included 0.708% w/w of sodium chloride, 0.470% w/w of boric acid, 0.05% w/w of sodium borate, 0.10% w/w of Example 1A (poly-MPC), and water as solvent.

Example 3D included 0.708% w/w of sodium chloride, 0.470% w/w of boric acid, 0.05% w/w of sodium borate, 0.005% w/w of vitamin B12, 0.10% w/w of Example 1A (poly-MPC), and water as solvent.

Example 3E included 0.708% w/w of sodium chloride, 0.470% w/w of boric acid, 0.05% w/w of sodium borate, 0.005% w/w of vitamin B12, 0.03% w/w of vitamin B6, 0.10% w/w of Example 1A (poly-MPC), and water as solvent Example 3F included 0.708% w/w of sodium chloride, 0.470% w/w of boric acid, 0.05% w/w of sodium borate, 0.03% w/w of vitamin B6, 0.10% w/w of Example 1A (poly-MPC), and water as solvent.

Experiment 4: Etafilcon A Lens Treated with Different Lens Storage Solutions

This experiment was performed by immersing etafilcon A lenses in the storage solutions of Comparative Examples 3A-3B and Examples 3C-3F respectively. Monomers for forming etafilcon A lenses included 2-hydroxyethyl methacrylate (HEMA), methacrylic acid (MAA), ethylene glycol dimethacrylate (EGDMA), 1,1,1-trimethylolpropane trimethacrylate (TMPTMA), and about 0.8% of UV blocking monomer, 2(2-hydroxy-5-methacryloxyethylphenyl)-2H-benzotriazole. These monomers were solidified in molds to form lenses. The lenses can be designed to have different curvatures by cast molding with different shapes of polypropylene molds. The formed lenses would have targeted optical powers ranging from −6.00 to −2.00 diopters, 8.5 mm base curve (BC), and 14.2 mm diameter. After proper hydration process, they were packed in polypropylene blisters with Comparative Examples 3A-3B and Examples 3C-3F, respectively. Subsequently, lenses were sterilized with autoclaving. These parameters and powers of the fully processed lenses would meet their targets and the fully processed lenses would have water content of 58%.

Experiment 5: Clinical Trials of Etafilcon A Lenses Treated by Different Storage Solution After satisfying the requirements of regulations of clinical trials, etafilcon A lenses treated by Comparative Example 3A (without poly-MPC), Comparative Example 3B (including hyaluronic acid) and Example 3D (including poly-MPC) respectively were tested in clinical trials. Over 30 subjects were instructed to wear lenses for at least 10 hours without leaving an air conditioned environment at a temperature of 25° C. and a humidity of 60%. The test included the following steps. On the first day, the subjects wore lenses treated by Comparative Example 3A the whole day. On the second day, the subjects wore lenses treated by Comparative Example 3B the whole day. On the third day, the subjects wore lenses treated by Example 3D the whole day. By alternatively wearing different treated lenses, the subjects could compare the comfort levels after wearing different treated lenses.

After wearing the lenses which had been immersed in Comparative Example 3A or Comparative Example 3B over 6 hours, over 70% of the subjects felt that their eyes are dry. However, under the same conditions, after the subjects wearing the lenses which had been immersed in Example 3D, no one felt dry. Such results obviously showed that the poly-MPC in storage solution could effectively keep lenses moist and prevent wearer's eyes from feeling dry. This result also proved that the moisturizing and anti-drying effects of the poly-MPC are much better than hyaluronic acid. Therefore, the copolymers formed by MPC would also effectively keep lenses moist and thus promote the comfort level of wearer. Moreover, even though the etafilcon A lenses include the UV blocking monomer, the copolymers formed by MPC would also effectively keep lenses moist and thus promote the comfort level of wearer.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A solution for treating contact lens, comprising:
about 0.01-1.0 parts by weight (pbw) of a polymer having phosphorylcholine groups, the polymer having a number-average molecular weight of about 4,000 to about 1,000,000 daltons, and the polymer consisting of a structure of formula (I):

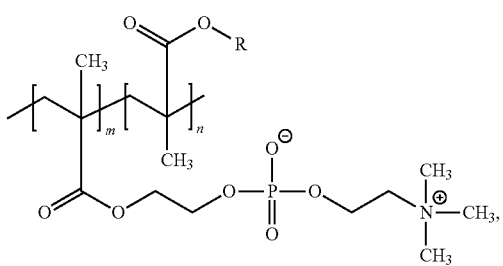

wherein, in formula (I), m is a positive integer, n is zero or a positive integer, R is $C_2$-$C_{12}$ hydroxyalkyl group, and m/n is greater than 1 when n is the positive integer;
about 0.001-0.1 pbw of vitamin B;
about 0.01-1 pbw of an inorganic salt; and
about 100 pbw of water.

2. The solution of claim 1, wherein the vitamin B is selected from the group consisting of vitamin B1, vitamin B2, vitamin B3, vitamin B6, and vitamin B12.

3. The solution of claim 2, wherein an amount of the vitamin B6 is in a range of about 0.01-0.1 pbw.

4. The solution of claim 2, wherein an amount of the vitamin B12 is in a range of about 0.001-0.1 pbw.

5. The solution of claim 1, wherein R is 2-hydroxyethyl or 2,3-dihydroxypropyl.

6. The solution of claim 1, wherein the inorganic salt comprises about 0.1-1 pbw of sodium chloride.

7. The solution of claim 6, further comprising about 0.1-1 pbw of boric acid.

8. The solution of claim 6, further comprising about 0.01-0.1 pbw of sodium borate.

9. The solution of claim 1, wherein the solution is a solution for storing contact lens or a solution for cleaning contact lens.

* * * * *